US00PP19548P2

(12) United States Plant Patent
Dirr

(10) Patent No.: US PP19,548 P2
(45) Date of Patent: Dec. 2, 2008

(54) ***LANTANA* PLANT NAMED 'CHAPEL HILL YELLOW'**

(50) Latin Name: ***Lantana* sp.**
Varietal Denomination: Chapel Hill Yellow

(75) Inventor: Michael Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 0 days.

(21) Appl. No.: 11/999,902

(22) Filed: Dec. 7, 2007

(51) Int. Cl.
*A01H 5/00* (2006.01)

(52) U.S. Cl. ..... Plt./227

(58) Field of Classification Search ..... Plt./227
See application file for complete search history.

*Primary Examiner*—Annette H Para
(74) *Attorney, Agent, or Firm*—Greenlee Winner and Sullivan, P.C.

(57) ABSTRACT

A new and distinct cultivar of *Lantana* plant named 'Chapel Hill Yellow', characterized by its low growing, layered and spreading growth habit; leathery, scabrous dark green foliage; continuous flowering; pale yellow flower buds that open to medium yellow with a darker yellow-orange center; and cold hardiness to USDA Hardiness Zone 7.

3 Drawing Sheets

Genus and species of plant claimed: *Lantana* sp.
Variety denomination: 'Chapel Hill Yellow'.

BACKGROUND OF THE INVENTION

The present invention relates to a new and distinct cultivar of *Lantana* plant, botanically known as *Lantana* sp., and hereinafter referred to by the cultivar name 'Chapel Hill Yellow'.

The new *Lantana* plant originated from a naturally occurring cross between *Lantana camara* 'Miss Huff' (not patented) and *Lantana×hybrida* 'New Gold' (not patented). The cultivar 'Chapel Hill Yellow' originated and was discovered in a cultivated environment at Chapel Hill, N.C., in summer 2004.

Asexual reproduction of the new cultivar by stem cuttings in Watkinsville, Ga. since summer 2005 has shown that all the unique features of this new *Lantana*, as herein described, are stable and reproduced true to type through successive generations of such asexual propagation.

SUMMARY OF THE INVENTION

Plants of the new cultivar 'Chapel Hill Yellow' have not been observed under all possible environmental conditions. The phenotype may vary somewhat with changes in light, temperature, soil and rainfall without, however, any variance in genotype.

The following traits have been repeatedly observed and are determined to be unique characteristics of 'Chapel Hill Yellow'. These characteristics in combination distinguish 'Chapel Hill Yellow' as a new and distinct cultivar: 1. Low growing, layered and spreading growth habit; 2. Leathery, scabrous dark green foliage; 3. Continuous flowering; 4. Pale yellow flower buds that open to medium yellow with a darker yellow-orange center; and 5. Cold hardiness to USDA Hardiness Zone 7.

Plants of the new *Lantana* 'Chapel Hill Yellow' differ from plants of the parent, 'Miss Huff', primarily in flower color and growth habit, as plants of 'Miss Huff' have orange, yellow, and pink flowers, and an upright spreading growth habit often reaching 90 to 150 cm high and wide. Plants of the new *Lantana* 'Chapel Hill Yellow' differ from plants of the parent, 'New Gold', primarily in flower color and cold hardiness, as plants of 'New Gold' have solid colored golden yellow flowers and lack consistent cold hardiness.

Plants of the new *Lantana* can be compared to plants of the cultivar 'New Gold'. However, in side-by-side comparisons conducted in Watkinsville, Ga., plants of the new *Lantana* differed from plants of the cultivar 'New Gold' in the following characteristics: 1. Plants of the new *Lantana* had darker green, thicker foliage than plants of the cultivar 'New Gold'; 2. Plants of the new *Lantana* had pale yellow flower buds that open to medium yellow with a darker yellow-orange center, whereas plants of the cultivar 'New Gold' had flower buds and flowers that were solid colored golden yellow; and 3. Plants of the new *Lantana* were consistently cold hardy from year to year, whereas plants of the cultivar 'New Gold' lacked consistent cold hardiness.

BRIEF DESCRIPTION OF THE DRAWINGS

The accompanying color photographs illustrate the flower and foliage characteristics and the overall appearance of the new *Lantana*, showing the colors as true as it is reasonably possible to obtain in color reproductions of this type. Colors in the photographs may differ slightly from the color values cited in the detailed botanical description which accurately describe the colors of the new *Lantana*.

DETAILED DESCRIPTION

Figure 1:
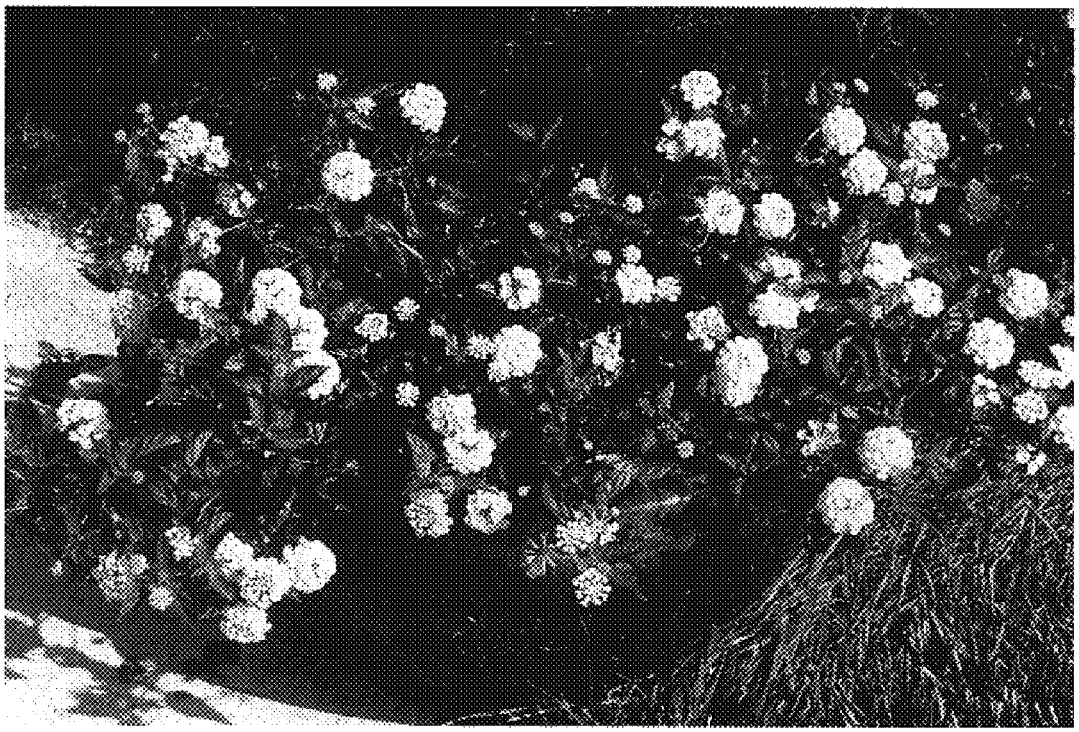
FIG. 1 illustrates the overall appearance of a mature plant of 'Chapel Hill Yellow'.
Figure 2:
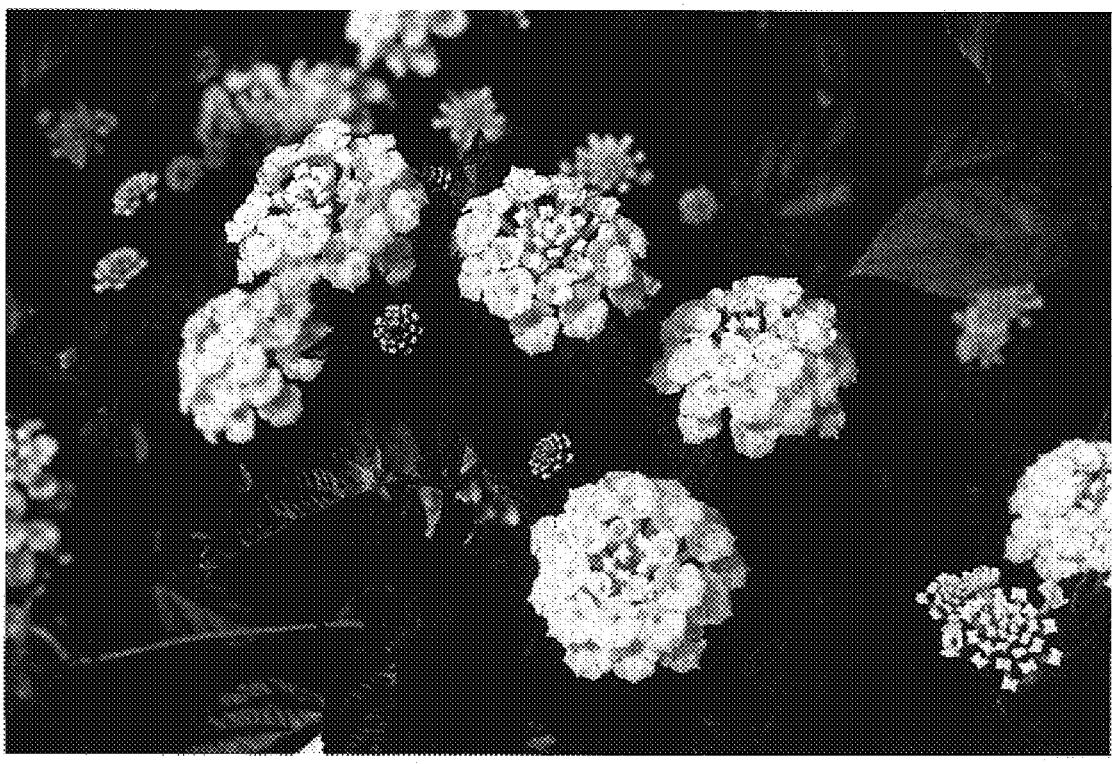
FIG. 2 illustrates a close-up view of the inflorescences of 'Chapel Hill Yellow'.
Figure 3:
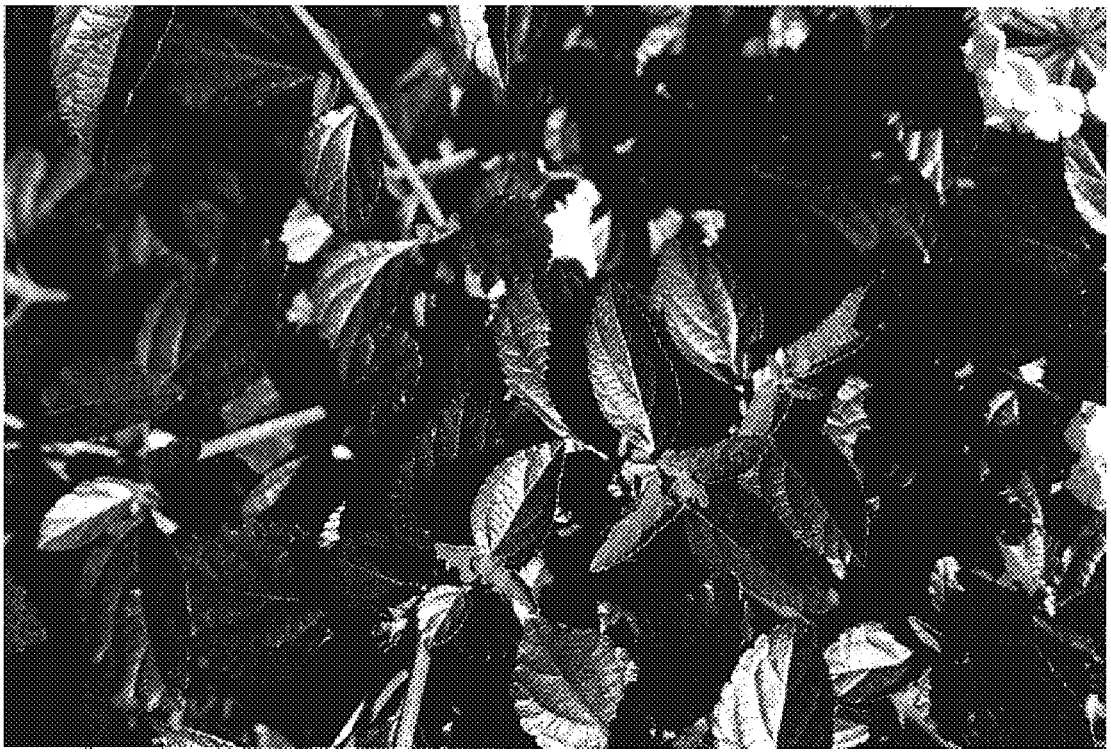
FIG. 3 illustrates a close-up view of the foliage of 'Chapel Hill Yellow'.

In the following description, color references are made to The Royal Horticultural Society Colour Chart, 2001 Edition, except where general terms of ordinary dictionary significance are used. Plants used for the description were grown in 11.8 L containers under outdoor conditions in a nursery in Watkinsville, Ga. Plants were about 6 months old when the description was recorded. Colors are described using The Royal Horticultural Society Colour Chart (R.H.S.).

Botanical classification: *Lantana* sp., cultivar 'Chapel Hill Yellow'.

Parentage:

*Female, or seed, parent.*—*Lantana camara* cultivar 'Miss Huff' (not patented).

*Male, or pollen parent.*—*Lantana×hybrida* cultivar 'New Gold' (not patented).

Propagation:

*Type cutting.*—Terminal cuttings.

*Time to initiate roots, summer.*—About 10 days at 32 C°.

Plant description: Perennial flowering plant; subshrub; low growing, layered and spreading growth habit. Freely branching; two lateral branches potentially forming at every node; pinching enhances lateral branch development.

*Root description.*—Numerous, fine, fibrous and well-branched.

*Plant height.* —About 41 cm. Plant diameter: about 150 cm. Lateral branches having a length of about 17 cm and a diameter of about 2.5mm. Shape: squarish.

*Internode length.*—About 5.7 cm.

*Strength.*—Strong, but flexible.

*Texture.*—Coarse, pubescent.

*Color* (*young*).—Close to 144A. Color (woody): close to 199A.

Foliage description:

*Arrangement.*—Opposite, simple. Length: about 4.2 cm. Width: about 2.9 cm. Shape: ovate. Apex: acute. Base: cuneate. Margin: crenate.

*Texture* (*upper surface*).—Leathery, moderately waxy, with scabrous pubescence.

*Texture* (*lower surface*).—Rough, with hispid pubescence.

*Venation pattern.*—Pinnate. Venation color (upper surface): close to 144A. Venation color (lower surface): close to 144A.

*Fragrance.*—Pungent, mint-like.

*Color in developing foliage* (*upper surface*).—Close to 137A. Color in developing foliage (lower surface): close to 138B. Color in fully expanded foliage (upper surface): close to 137A. Color in fully expanded foliage (lower surface): close to 137C.

*Petiole length.*—About 6 mm. Petiole diameter: about 2 mm. Petiole texture, both surfaces: hispid pubescence. Petiole color (upper surface): close to 143A. Petiole color (lower surface): close to 144A.

Flower description:

*Flower type and habit.*—Small salverform flowers arranged in axillary corymbs; flowers face mostly upward or outward. Flowers are self-cleaning. Freely flowering with potentially two inflorescences per node; typically about 29 flowers per corymb. Natural flowering season — spring until frost in the autumn; flowering is continuous. Flower longevity on the plant — about one week. Fragrance - faint, pleasant.

*Inflorescence diameter.*—About 3.5 cm. Inflorescence height: about 1.6 cm.

*Flower appearance.*—Flared trumpet, corolla fused, four-parted; flowers roughly rectangular in shape. Diameter: about 9 mm by 14 mm. Corolla tube length: about 1.4 cm.

*Flower bud.*—Length: about 6 mm; Diameter: about 2 mm; Shape: oblong; Color: close to 12C.

*Pedicels.*—Not observed, flowers not stalked.

Petals:

*Arrangement/appearance.*—Single whorl of four petals, fused into flared trumpet.

*Petal length from throat.*—About 4.5 mm for upper and lower petals and about 3 mm for lateral petals.

*Petal width.*—Upper and lower petals are about 7 mm. Lateral petals are about 3.5 mm.

*Petal shape.*—Spatulate to somewhat orbicular. Petal apex: obtuse. Petal base: fused. Petal margin: entire. Petal texture, upper and lower surfaces: smooth, glabrous.

*Color of petal lobes, when opening and fully opened, upper surface.*—Close to 3D. Color of petal lobes, when opening and fully opened, lower surface: close to 5D. Color of throat: close to 16A. Color of tube: close to 13C.

Sepals:

*Arrangement/appearance.*—One sepal per flower at the base of the corolla, leaf-like. Length is about 5 mm. Width is about 1 mm. Shape: lanceolate. Apex: acute. Margin: entire. Texture, upper and lower surface: scabrous.

*Color, upper and lower surfaces.*—Close to 144A.

Peduncles: Length is about 4.3 cm. Diameter is about 2 mm. Angle: about 45 degrees from the stem. Strength: flexible, but strong. Color: close to 144A.

Stamens:

*Quantity/arrangement.*—Four per flower, adnate to the inside of the corolla tube. Anther shape: oblong. Anther length: less than 1 mm. Anther color: close to N199B. Pollen amount: none observed.

Pistils:

*Quantity.*—One per flower. Pistil length: about 2.5 mm. Stigma shape: rounded. Stigma color: close to 145A. Style color: close to 145A. Ovary color: close to 145A.

Fruit:

*Type/appearance.*—Drupe. Shape: round. Diameter: about 5 mm. Mature color: 202A. Number per Infructescence: about 5.

Disease/pest resistance: Plants of the claimed *Lantana* variety grown in the garden have not been noted to be resistant to pathogens and pests common to *Lantana*.

Weather and temperature tolerance: Plants of the new *Lantana* variety have been observed to be tolerant to rain and wind, and have been observed to be tolerant to temperatures ranging from about 0 degrees C. to about 38 degrees C. and are hardy to about USDA Hardiness Zone 7.

I claim:

1. A new and distinct *Lantana* plant named 'Chapel Hill Yellow', as illustrated and described herein.

* * * * *